(12) United States Patent
Amr et al.

(10) Patent No.: US 10,343,997 B1
(45) Date of Patent: Jul. 9, 2019

(54) URSOLIC ACID DERIVATIVES

(71) Applicant: KING SAUD UNIVERSITY, Riyadh (SA)

(72) Inventors: Abd El-Galil E. Amr, Riyadh (SA); Mohamed A. Al-Omar, Riyadh (SA); Abdulrahman A. Almehizia, Riyadh (SA); Mohammed Mater Alanazi, Riyadh (SA); Nawaf Abdulaziz Alsaif, Riyadh (SA); Ahmad Jomah Obaidullah, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/208,849

(22) Filed: Dec. 4, 2018

(51) Int. Cl.
*C07D 213/02* (2006.01)
*C07D 211/90* (2006.01)
*A61P 9/12* (2006.01)

(52) U.S. Cl.
CPC ............. *C07D 211/90* (2013.01); *A61P 9/12* (2018.01)

(58) Field of Classification Search
CPC .................................................. C07D 213/02
USPC ................................................. 546/318, 255
See application file for complete search history.

(56) References Cited

U.S. PATENT DOCUMENTS

| 6,545,028 | B2 | 4/2003 | Jensen et al. |
| 8,802,661 | B2 | 8/2014 | Regueiro-Ren et al. |
| 9,657,029 | B2 | 5/2017 | Sun |
| 2015/0272922 | A1 | 10/2015 | Durst et al. |

FOREIGN PATENT DOCUMENTS

| CN | 102180939 B | 2/2013 |
| CN | 103739654 A | 4/2014 |
| CN | 103694375 B | 10/2016 |
| CN | 106362157 A | 2/2017 |
| WO | 2012106188 A1 | 8/2012 |
| WO | 20120170546 A1 | 12/2012 |

OTHER PUBLICATIONS

Karliner et al., Journal of Organic Chemistry (1966), 31(6), 1945-56.*
Clapham, John C. "A method for in vivo assessment of calcium slow channel blocking drugs." Journal of cardiovascular pharmacology 11.1 (1988): 56-60.
Vaghy, Pal L., et al. "Effects of Bay k 8644, a dihydropyridine analog, on [3H] nitrendipine binding to canine cardiac sarcolemma and the relationship to a positive inotropic effect." Circulation research 55.4 (1984): 549-553.
Schmid, Annie, et al. "The nitrendipine-sensitive Ca2+ channel in chick muscle cells and its appearance during myogenesis in vitro and in vivo." Journal of Biological Chemistry 259.18 (1984): 11366-11372.
Woźniak, Łukasz, Sylwia Skąpska, and Krystian Marszalek. "Ursolic acid—a pentacyclic triterpenoid with a wide spectrum of pharmacological activities." Molecules 20.11 (2015): 20614-20641.
Somova, L. O., et al. "Cardiovascular, antihyperlipidemic and antioxidant effects of oleanolic and ursolic acids in experimental hypertension." Phytomedicine 10.2-3 (2003): 115-121.
Kim, Mikyung, Chang-ho Han, and Moo-Yeol Lee. "Enhancement of platelet aggregation by ursolic acid and oleanolic acid." Biomolecules & therapeutics 22.3 (2014): 254.
Shao, Jing-Wei, et al. "In vitro and in vivo anticancer activity evaluation of ursolic acid derivatives." European journal of medicinal chemistry 46.7 (2011): 2652-2661.
Huang, Mou-Tuan, et al. "Inhibition of skin tumorigenesis by rosemary and its constituents carnosol and ursolic acid." Cancer research 54.3 (1994): 701-708.
Furtado, Ricardo A., et al. "Ursolic acid and oleanolic acid suppress preneoplastic lesions induced by 1, 2-dimethylhydrazine in rat colon." Toxicologic pathology 36.4 (2008): 576-580.
Liu, Wenbo, et al. "Ursolic acid inhibits cigarette smoke extract-induced human bronchial epithelial cell injury and prevents development of lung cancer." Molecules 17.8 (2012): 9104-9115.
Gayathri, Renganathan, et al. "Ursolic acid attenuates oxidative stress-mediated hepatocellular carcinoma induction by diethylnitrosamine in male Wistar rats." Asian Pac J Cancer Prev 10.5 (2009): 933-8.
Zeng, Guang, et al. "Ursolic acid inhibits T-cell activation through modulating nuclear factor-κ B signaling." Chinese journal of integrative medicine 18.1 (2012) 34-39.
Anand, Krishnan, et al. "Design, synthesis, anticancer, antimicrobial activities and molecular docking studies of novel guinoline bearing dihydropyridines." Journal of Photochemistry and Photobiology B: Biology 165 (2016): 266-276.

(Continued)

*Primary Examiner* — Niloofar Rahmani
(74) *Attorney, Agent, or Firm* — Richard C. Litman

(57) ABSTRACT

An ursolic acid derivative can have the following structural formula:

The ursolic acid derivative exhibits potent selective calcium channel blocker activities and may be used to treat a disease or condition for which calcium channel regulation is useful.

11 Claims, No Drawings

(56) References Cited

OTHER PUBLICATIONS

Kumar, R. Surendra, et al. "Synthesis and anticancer activity of some new series of 1, 4-dihydropyridine derivatives." (2011).
Bladen, Chris, et al. "1, 4-Dihydropyridine derivatives with T-type calcium channel blocking activity attenuate inflammatory and neuropathic pain." Pflügers Archiv-European Journal of Physiology 467.6 (2015): 1237-1247.
Schotte, Alain, et al. "In vitro receptor binding and in vivo receptor occupancy in rat and guinea pig brain: risperidone compared with antipsychotics hitherto used." The Japanese Journal of Pharmacology 69.4 (1995): 399-412.
Zonouz, Adeleh Moshtaghi, and Nahid Sahranavard. "Synthesis of 1, 4-dihydropyridine derivatives under aqueous media." Journal of Chemistry 7.S1 (2010): S372-S376.
Curtis, Tim M., and C. Norman Scholfield. "Nifedipine blocks Ca2+ store refilling through a pathway not involving L-type Ca2+ channels in rabbit arteriolar smooth muscle." The Journal of physiology 532.3 (2001): 609-623.
Mahmoudian, M., et al. "Synthesis and Biological activity of two new calcium-channel blockers, mebudipine and dibudipine," Journal of pharmacy and pharmacology 49.12 (1997): 1229-1233.
Lowry, Oliver H., et al. "Protein measurement with the Folin phenol reagent." Journal of biological chemistry 193.1 (1951): 265-275.

* cited by examiner

URSOLIC ACID DERIVATIVES

BACKGROUND

1. Field

The disclosure of the present patent application relates to ursolic acid derivatives, and more specifically, to ursolic acid derivatives functionalized with a dihydropyridine moiety at the C28 position, methods of synthesizing such compounds, and use of such compounds as calcium channel blockers.

2. Description of the Related Art

Calcium ions play an essential role in regulating skeletal and smooth muscle contractility and in the performance of normal and diseased hearts. Calcium channel blockers are particularly effective against large vessel stiffness, a common cause of elevated systolic blood pressure in elderly patients. Calcium channel blockers also directly influence biosynthesis of aldosterone in adrenocortical cells. Ursolic acid is one of the most promising biologically derived substances for use in a range of potential biomedical applications, including cancer therapy and prevention, anti-hyperlipidemic, antioxidant activities, and platelet enhancement. For example, several tests have demonstrated anti-carcinogenic activity of ursolic acids against different induction sources. Additionally, ursolic acid prevents development of severe hypertension. Its antihypertensive activity presumably arises from its direct effects on cardiac function (heart rate decrease by 32%).

Nifedipine is a calcium channel blocker and medication used to treat angina, high blood pressure, and severe high blood pressure in pregnancy. Although Nifedipine and other dihydropyridine derivatives are commonly regarded as specific to L-type calcium channel blocker, they also possess nonspecific activity towards other voltage-dependent calcium channels.

Thus, an ursolic acid derivative solving the aforementioned problems is desired.

SUMMARY

An ursolic acid derivative includes a compound having the chemical structure shown below

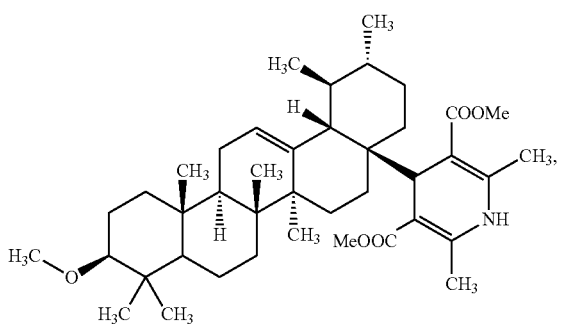

or a pharmaceutically acceptable salt thereof.

These and other features of the present disclosure will become readily apparent upon further review of the following specification and drawings.

DETAILED DESCRIPTION OF THE PREFERRED EMBODIMENTS

An ursolic acid derivative includes a compound having the chemical structure shown below

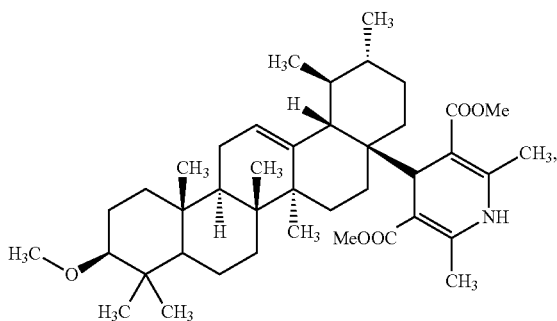

or a pharmaceutically acceptable salt thereof.

Scheme 1 below depicts an exemplary reaction scheme by which the ursolic acid derivative can be prepared.

Scheme 1

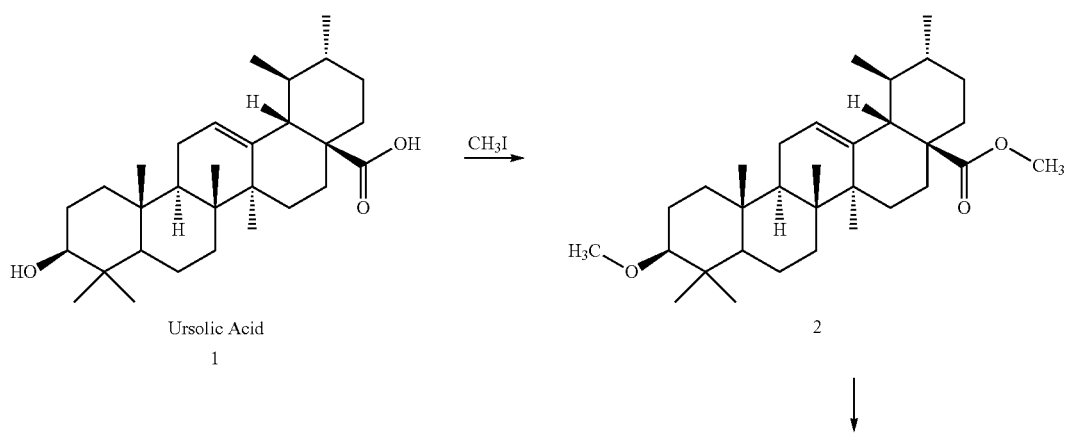

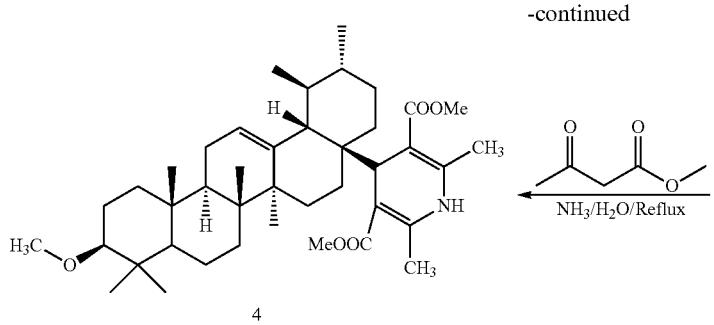

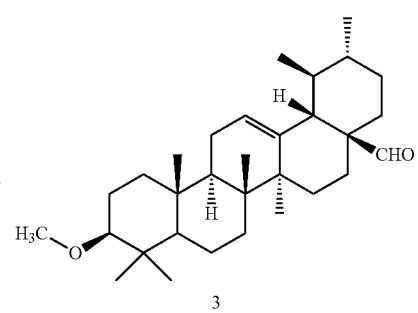

As shown in Scheme 1, both the C3 hydroxyl group and the C28 acetoxy group of ursolic acid are methylated by reacting the ursolic acid 1 with methyl iodide in dry acetone in the presence of potassium carbonate to provide the corresponding 3-methoxy ursolic methyl ester 2, which is then reduced by addition of potassium diisobutyl-t-butoxy aluminum hydride (PDBBA) [Chae et al., 2007; Zonouz et al., 2010] to give the corresponding aldehyde derivative 3. The ursolic acid derivative 4 is obtained by a one-pot reaction of aldehyde derivative 3, methyl acetoacetate and ammonia water under refluxing conditions.

The ursolic acid derivative of the present teachings includes a symmetric dihydropyridine moiety at the C28 position, which is believed to be at least partly responsible for the calcium channel blocking activities of the ursolic acid derivative. As described in detail herein, the ursolic acid derivative is more potent at blocking selective calcium channel activities and more effective in reducing electrically and chemically induced contractile responses of guinea pig and rat than Nifedipine. For example, the ursolic acid derivative can be an effective L-type calcium channel blocker.

The ursolic acid derivative can be used as an active ingredient in a pharmaceutical composition useful as a calcium channel blocker, for treatment of diseases typically ameliorated by calcium channel blockers and/or antihypertension drugs. A pharmaceutical composition can include the ursolic acid derivative, or salt thereof, and a pharmaceutical carrier. The pharmaceutical composition including the ursolic acid derivative can be prepared and administered in any suitable manner. In an embodiment, the pharmaceutical composition can be prepared by intimately admixing the ursolic acid derivative or salt thereof with a pharmaceutical carrier according to conventional pharmaceutical compounding techniques. Carriers are inert pharmaceutical excipients, including, but not limited to, binders, suspending agents, lubricants, flavorings, sweeteners, preservatives, dyes, and coatings. The pharmaceutical composition can be administered by any conventional route of administration, including, but not limited to, intravenous, oral, subcutaneous, intramuscular, intradermal and parenteral.

The following examples are provided by way of illustration.

Example 1

Synthesis of the Ursolic Acid Derivative

All reported melting points (mp) are reported as uncorrected values and were measured using an electrothermal capillary melting point apparatus. IR spectra were recorded on a Shimadzu FT-IR 8101 PC infrared spectrophotometer. The $^1$H-NMR spectra were determined using a Bruker AM-200 MHz spectrometer. The chemical shifts are expressed on the δ (ppm) scale using tetramethylsilane (TMS) as the standard reference. Mass spectra were recorded a on a Finnigan SSQ liquid chromatography-mass spectrometry system operating at 70 eV. Elemental analysis was determined on a Perkin Elmer 240 Elemental Analyzer (microanalysis), Microanalysis Center, Cairo University, Cairo, Egypt.

Synthesis of methyl-3-βmethoxy-ors-12-en-28-oate (2)

A reaction mixture of ursolic acid (3 g, 6.6 mmol) was dissolved in dry acetone (350 ml). Anhydrous potassium carbonate (16 g) and methyl iodide (about 40 g) was added to the reaction mixture. The reaction mixture was then refluxed in a water-bath and maintained at a temperature of ranging from 25° C.-28° C., for about 80 hours. Alternatively, the reaction progress may be monitored by thin layer chromatography (TLC). To the reaction mixture, a small quantity of methyl iodide was added every day to make up for reagent lost through evaporation. The reaction mixture was then evaporated to obtain a residue, which was dissolved in methyl ether and washed with water to remove any potassium salts formed. The methyl ether solution was dried on sodium sulfate, filtered off, evaporated and crystallized from dilute alcohol to obtain methyl-3-β-methoxy-urs-12-en-28-oate 2.

Synthesis of 3-β-methoxy-urs-12-en-28-aldehyde (3)

A solution of methyl-3-β-methoxy-urs-12-en-28-oate 2 (2.42 g, 5 mmol) in tetrahydrofuran (THF) (50 mL) was made containing naphthalene as an internal standard. PDBBA [16] (13 mL, 5 M in THF/hexane) was added and the resulting solution was cooled to 0° C. After allowing the mixture to react at 0° C. for 24 h, or as long as required for the reaction to be determined to be completed by TLC, the reaction mixture was hydrolyzed with hydrochloric acid (HCl, 50 mL, 1 N) and the product was extracted with addition of diethyl ether (100 mL). The ether layer was dried over anhydrous magnesium sulfate to give the corresponding aldehyde 3.

Dihydropyridine-3,5-dicarboxylate Ursolic Acid Derivative (Compound 4)

A mixture of aldehyde 3 (3.67 mmol, 1.77 g), methyl acetoacetate (1 mL), and 25% ammonia (3.67 mmol, 0.27 mL) in the presence of montmorillonite K10 (20 wt %, 34 mg) as catalyst in water (20 mL) was refluxed for 48 h or until the reaction was determined to be sufficiently completed by TLC. After the reaction completed, the reaction mixture was evaporated to obtain a solid product, which was crystallized from ethanol to give compound 4.

Results of Synthesis of Compound 4:

Yield 67%, mp. 222, [a]; =+170 (c 1, CHCb); IR (KBr, cm-1): 3454 (NH), 2980 (CH, aliphatic), 1738 (ester), 1648 (C=C), 1270 (ether). 1 H-NMR (CDCb, δ ppm): 0.85 (d, 1H, CH), 0.88 (s, 3H, CH3), 0.92 (d, 3H, Cl-I3), 0.96 (d, 1H, CH), 1.00 (s, 31-I, CH3), 1.04 (d, 311, Cl-h), 1.08 (m, 1H, CH), 1.12 (s, 3H, CH3), 1.16 (m, 1H, CH), 1.20 (s, 3H, CH3), 1.24 (s, 3H, CII3), 1.30 (m, 1H, CH), 1.35 (m, 1H, CH), 1.39 (m, 1H, CH), 1.44 (m, 1H, CH), 1.48 (m, 1H, CH), 1.52 (d, 1H, CH), 1.56 (m, 1H, CH), 1.60 (m, 1H, CI-I), 1.64 (s, 1H, CH), 1.80 (dd, 21-1, CI-12), 1.90 (m, 2H, CH2), 1.95 (m, 1H, CH), 1.99 (m, 1H, CI-1), 2.04 (m, 1H, CH), 2.14 (tr, 1H, CI-I), 2.34 (s, 6H, 2CH3), 2.34 (tr, 1H, CH), 2.64 (d, 1H, CH), 3.34 (s, 3H, OCH3), 3.45 (dd, 1H, CH), 3.71 (s, 6H, 2COOCH3), 5.50 (s, 11H, CH), 5.75 (s, 1H, CH), 8.15 (s, 1H, NH). 13C-NMR (CDCh, 8 ppm): 15.90, 16.78, 17.66, 17.89, 18.67, 18.80, 21.34, 23.54, 24.98, 25.66, 28.52, 28.55, 28.74, 31.57, 33.54, 33.86, 37.76, 37.82, 39.34, 39.45, 39.48, 39.90, 40.67, 42.48, 48.54, 48.89, 50.16, 53.78, 55.36, 59.18, 78.34, 103.40, 125.46, 139.75, 145.10, 268.19 (41 C). MS (EI): m/z 650 (100%) [M+]. Anal. Calcd for C41 H 63N0:1 (649.94): Calcd C, 75.77; H, 9.77; N, 2.16. Found C, 75.70; 1-I, 9.70; N, 2.10.

Example 2

Assessments of Bioactivities of the Ursolic Acid Derivative

Effects of Compound 4 and Nifedipine on Isolated Guinea-Pig Ileums

Male guinea-pigs, weighing between 200-400 g, were killed by a blow on the head after previously being deprived of food for 18 h but having had free access to water. The non-terminal part of the ileum was removed and cut into 20-mm long segments, which were suspended in an organ bath and connected to an isotonic transducer. The organ bath contained 50 mL physiological solution oxygenated with 95% $O_2$ and 5% $CO_T$ at 37° C. The physiological solution was typically normal saline with 0.9% sodium chloride. The fluid of the organ bath was changed every 15 min. The ileal segments were subjected to a resting tension of 0.5-1 g and left to equilibrate for 60 min.

To study the effects of compound 4 and Nifedipine on electrically induced contraction of ileal tissue, the ilial tissue was suspended in physiological solution (composition mM: NaCl 136.9, KCl 2.68, $MgCl_2$ 1.05, $CaCl_2$ 1.8, $NaH_2PO_4$ 1, $NaHCO_3$ 11.9, glucose 5.5) and stimulated with a Harvard stimulator (stimulation specification: 25V, 0.1 Hz, pulse-width 5 ms) via a bipolar platinum electrode. Cumulative doses of either compound 4 or Nifedipine were then added to the organ bath at 10-min intervals. Each segment was treated with only one compound. The $pIC_{50}$ ($-\log IC_{50}$) value of each compound was calculated from concentration-response curves.

Compound 4 and Nifedipine concentration-dependently reduce electrically evoked contractile responses of guinea pig ileum (see Table 1), but compound 4 much more potently reduced contractility relative to Nifedipine. The highest percentage of ethanol which was obtained in organ bath was 0.1%, which had no significant effect on the electrically induced contractions. Table 1 depicts $pIC_{50}$ ($-\log IC_{50}$) for relaxation of electrically induced contraction by compound 4 and Nifedipine of guinea-pig isolated ileum and potassium-induced contraction of rat isolated aorta. In rat aorta, the $pIC_{50}$ values of compound 4 and Nifedipine were significantly different (P<<0.001).

TABLE 1

| $pIC_{50}$ ($-\log IC_{50}$) for relaxation of electrically induced contraction | | |
|---|---|---|
| | Compound 4 | Nifedipine |
| Ileum* | 9.46 ± 0.02 | 7.45 ± 0.27 |
| Aorta* | 10.76 ± 0.03 | 8.29 ± 10.07 |

Values are means ± standard error (± s.e.); n = 6.

To study the effects of compound 4 and Nifedipine on calcium-induced contractions, the tissue was suspended in a modified calcium-free, high potassium physiological solution (composition mM: NaCl 97, KCl 40, $NaH_2PO_4$ 0.4, $NaHCO_3$ 11.9, glucose 5.5). As a control, increasing concentrations of $CaCl_2$ (0.1, 0.3, 1, 3, 10 mmol) were added to an organ bath and the contractile response of the ileum was recorded. Tissues were then preincubated for 15-20 min with one concentration of each calcium channel blocker and increasing concentrations of $CaCl_2$ were again added to the bathing media. Tissues were incubated with three concentrations of compound 4 and Nifedipine. Each segment was treated with only one of compound 4 or Nifedipine. To compare the inhibitory effects of compound 4 and Nifedipine, the response percentage ratio of the calcium channel blocker, i.e., the ratio of the percent of a maximum response induced by a particular concentration of calcium in the presence of a certain concentration of the calcium-channel blocker and in the absence thereof), was calculated and compared [Mahmoudian et al., 1997].

Re-treatment of K+-depolarized rat ileum tissue with compound 4 and Nifedipine, respectively, resulted in a shift to the right of the initial calcium dose-response curves. To compare the inhibitory effect of compound 4 and Nifedipine, the effect of $2 \times 10^{-9}$ M of each compound on contractions induced by 3 mM calcium was measured. This dose of calcium produces 84.44% (±0.96%) of a maximum response of said tissue in the absence of calcium antagonists. Compound 4 and Nifedipine reduced calcium-induced contractions to 27% (±1.8) and 74% (±6) of the maximum response, respectively.

Response percentage ratios were calculated by dividing the percent of maximum responses induced by 3 mM calcium in the presence of each calcium-channel blocker at a concentration of $2 \times 10^{-9}$ M by the percent of maximum response induced by 3 mM calcium in the absence of any calcium-channel blocker. As shown in Table 2, the response percentage ratio of compound 4 differs significantly from that of Nifedipine (P<0.001) on the calcium-induced contraction in guinea pig ileum. In other words, compound 4 has a greater inhibitory effect on calcium-induced contractions relative to Nifedipine.

TABLE 2

| Percentage Ratio of Compound 4 and Nifedipine on Calcium-Induced Contraction in guinea-pig ileum | | |
|---|---|---|
| | Compound 4 | Nifedipine |
| Response percentage ratio* | 0.15 ± 0.009 | 0.90 ± 0.07 |

Effects of Compound 4 and Nifedipine on Isolated Rat Aorta

Six white male rats were killed by a blow on the head and decapitation. The thoracic aorta of each rat was isolated, carefully dissected from the surrounding tissues, and cut into 5 segments, 3 mm in length. The segments were joined together, suspended in Krebs solution (composition in mmol: NaCl 118, KCl 4.8, $CaCl_2$, 2.5, $KH_2PO_4$ 1.2, $MgSO_4$ 1.2, $NaHCO_3$ 25 and glucose 10) at 37° C. and oxygenated with 95% $O_2$ and 5% $CO_2$. The fluid of the organ bath was changed every 15 min. The tissue was subject to a resting tension of 1 g and left to equilibrate for 1 h. The contractions of isolated aortic rings were recorded by means of a force transducer and Beckman physiograph. To study the vasodilatory effects of compound 4 and Nifedipine, the aorta tissue was pre-contracted with KCl (40 mM in water) such that the tissue was not pre-contracted more than 10%. The pre-contracted tissue was then subject to increasing amounts of one of the calcium channel blockers added to the organ bath. The $pIC_{50}$ value of each compound was calculated from concentration-response curves.

Isolated rat aortic rings were pre-contracted with 40 mM KCl and then relaxed by treatment with compound 4 or Nifedipine. The observed $pIC_{50}$ of compound 4 was significantly greater than that of Nifedipine (Table 1, P<0.0001). Therefore, in rat isolated aorta, compound 4 shows greater potency relaxing $K^+$-induced contractions relative to Nifedipine.

Calcium Channel Blocking Activity

In Vitro $^3$H-Nitrendipine Binding Assay

Radiolabeled dihydropyridine calcium channel antagonists such as $^3$H-nitrendipine are selective ligands for drug receptor sites associated with the voltage-dependent calcium channel. A constant concentration of the radioligand $^3$H-nitrendipine (0.3-0.4 nM) was incubated with increasing concentrations of a non-labeled test drug (0.1 nM-1 mM) in the presence of plasma membrane from bovine cerebral cortices. If the test drug exhibits any affinity to calcium channels, it is able to compete with the radioligand for channel binding sites.

Two freshly-slaughtered bovine brains were obtained from the slaughter house and placed in ice-cold preparation buffer comprising phosphate buffer. In the laboratory, approximately 5 g wet weights of the two frontal cerebral cortices were separated from the brains for further testing.

As shown in Table 3, Compound 4 showed greater binding affinity to calcium channels than Nifedipine.

TABLE 3

The affinity constant Ki [mol/1] of compound 4 and Nifedipine using an in vitro $^3$H nitrendipine binding assay

| Compound | The affinity constant Ki [mol/1] |
|---|---|
| Compound 4 | $3.1 \times 10^{-13}$ |
| Nifedipine | $2.4 \times 10^{-9}$ |

For the in vitro $^3$H-nitrendipine binding assay, the materials and solutions used were as follows: Tris-HCl 50 mM pH 7.4 preparation buffer; Tris-HCl 50 mM incubation buffer used was; Genapol 0.001% pH 7.4; and Radioligand $^3$H-nitrendipine; specific activity 2.59-3.22 TBq/mmol (70-87 Ci/mmol) (New England Nuclear). For inhibition of $^3$H-nitrendipine binding in non-specific binding experiments, Nifedipine (Sigma) was used.

For membrane suspension preparation, the tissue was homogenized (glass Teflon potter) in ice-cold preparation buffer, corresponding to 1 g cerebral wet weight/50 ml buffer, and centrifuged at 48,000 g, 4° C., for 10 min. The resulting pellets were re-suspended in approximately 270 ml preparation buffer to form a homogenate, and the homogenate was centrifuged as before. The final pellets were dissolved in preparation buffer, corresponding to 1 g cerebral cortex wet weight/30 ml buffer. The membrane suspension was immediately stored in aliquots of 5-10 ml at −77° C. Protein content of the membrane suspension was determined according to the method of Lowry et al. (1951) with bovine serum albumin as a standard.

On the day of the experiment, the required volume of the membrane suspension was slowly thawed and centrifuged at 48,000 g, 4° C., for 10 min. The resulting pellets were re-suspended in a volume of ice-cold incubation buffer, yielding a membrane suspension with a protein content of 0.6-0.8 mg/ml. After homogenization (glass Teflon potter), the membrane suspension was stirred under cooling at around 0° C. for 20-30 min until the start of the experiment.

As 1,4-dihydropyridines tend to bind to plastic material, all dilution steps were performed in glass tubes. For each concentration tested, samples were prepared in triplicate. The total volume of each incubation sample is 200 µL (micro titer plates). In the saturation experiments, for total binding, 50 µL $^3$H-nitrendipine (12 concentrations, $5\times10^{-11}$-$4\times10^{-9}$ M), and 50 µL incubation buffer were used. For non-specific-binding, 50 µL $^3$H-nitrendipine (4 concentrations, $5\times10^{-11}$-$4\times10^{-9}$ M) and 50 µL Nifedipine ($5\times10^{-7}$ M) were used. For competition experiments, 50 µL $^3$H-nitrendipine (1 constant concentration, $3$-$4\times10^{-10}$ M) and 50 µL incubation buffer without or with non-labeled test drug (15 concentrations, $10^{-10}$-$10^{-3}$ M) were used.

The binding reaction was started by adding 100 µL membrane suspension per incubation sample (0.6-0.8 mg protein/ml). The samples were incubated for 60 min in a bath shaker at 25° C. The reaction was stopped by subjecting the total incubation volume to rapid vacuum filtration over glass fiber filters. The membrane-bound radioactivity was thereby separated from the free radioactivity. Filters were washed immediately with approx. 20 ml ice-cold rinse buffer per sample. The retained membrane-bound radioactivity on the filter was measured after addition of 2 ml liquid scintillation cocktail per sample in a Packard liquid scintillation counter.

For evaluating the saturation experiments, the following parameters were calculated: total binding; non-specific binding; and specific binding=total binding−non-specific binding.

The dissociation constant (Ki) of the test drug was determined from the competition experiment of $^3$H-nitrendipine versus non-labeled drug by a computer-supported analysis of the binding data. The affinity constant $K_i$ [mol/L] of the test drug was defined as the concentration at which 50% of the receptors are occupied by the test drug. The $K_i$ value serves as a parameter to assess the efficacy of the test drug as a calcium channel blocker. Standard data: Nifedipine $K_i=2.4\times10^9$ mol/L.

Calcium blockers in the pithed rat were calculated in vivo. The cardio accelerator response in pithed rats distinguishes calcium entry blockers from other agents which have modes of action not involving direct blockade of calcium entry [Clapham, 1988].

Male Sprague-Dawley rats (250-350 g) were anaesthetized with methohexitone sodium (50 mg/kg, intraperitoneal injection). Following cannulation of the trachea, the rats were pithed through one orbit with a stainless steel rod and immediately artificially respired with room air (78 strokes/min, 1 mil/100 g body weight) via a Palmer small animal respiration pump. A jugular vein was cannulated for administration of drugs. Arterial blood pressure was recorded from a carotid artery using a pressure transducer.

Heart rate was derived from the phasic arterial pressure signal with a phase lock loop ratemeter (BRL Instrument Services). Both heart rate and arterial pressure were displayed on a recorder. The animals were kept warm by an incandescent lamp positioned about 25 cm above them. The pithing rod was withdrawn until the tip reached the thoracic portion of the spinal cord. All rats then received (+)tubocurarine (1.5 mg/kg, intravenously) and were bilaterally vagotomized.

The cardio accelerator response was obtained by continuous electrical stimulation of the thoracic spinal cord with square wave pulses of 0.5 ms duration, at supramaximal voltage at a frequency of 0.5 Hz using the pithing rod as a stimulating electrode. An indifferent electrode was inserted subcutaneously in the femoral region. Only rats with a resulting tachycardia of more than 100 beats/min were included in the experiments. When the cardio accelerator response was stabilized for about 3-5 min, cumulative intravenous doses of test drug or corresponding vehicle were administered. Successive doses were given when the response to the previous dose stabilized. Calcium antagonists and β-blockers inhibited the tachycardia elicited by electrical stimulation of the spinal cord dose dependently, whereas lignocaine and nicorandil provided no effect.

Doses of β-blockers or calcium-antagonists, which reduce the tachycardia to 50%, were tested again. Three minutes after administration of the drug, calcium gluconate (1 mg/min) or water (0.1 ml/min) was infused using a Harvard apparatus compact infusion pump. The effects of calcium entry blockers, but not of β-adrenoreceptor blockers, were antagonized.

The level of tachycardia immediately prior to drug administration was taken as 100% and responses to drugs were calculated as a percentage of the predose tachycardia. If an inhibitory effect of >50% was seen, then an $ID_{50}$ (with 95% confidence limits) was interpolated from linear regression analysis. Significance of differences between the groups receiving calcium gluconate and their parallel vehicle controls were calculated by a Student's t-test.

Results were expressed as means±standard error (s.e.). Differences between the $pIC_{50}$ and response percentage ratio values of the test compounds in each preparation were compared using a two-tailed Student t-test to determine significance. A P value<0.05 was considered to be indicative of significance.

It was found that cardio accelerator response in pithed rats allows for calcium entry blockers to be distinguished from other agents which have modes of action not involving a direct blockade of calcium entry. The results of such assays performed as described herein show that compound 4 is a selective calcium channel blocker and more potent than Nifedipine. Table 4 shows $ID_{50}[\mu M]$ of compound 4 and Nifedipine determined by in vivo evaluation of calcium blockade in the pithed rat.

TABLE 4

| $ID_{50}$ [μM] of compound 4 and Nifedipine | |
|---|---|
| Compound | $ID_{50}$ [μM] |
| Compound 4 | 71.62 |
| Nifedipine | 112.34 |

It is to be understood that the ursolic acid derivatives is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An ursolic acid derivative comprising the following structural formula

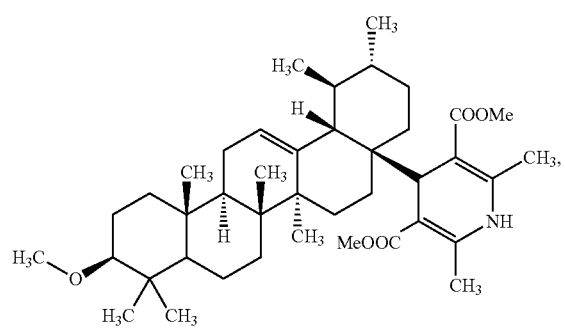

or a pharmaceutically acceptable salt thereof.

2. A pharmaceutical composition, comprising the ursolic acid derivative according to claim 1 and a pharmaceutically acceptable carrier.

3. A method of treating hypertension, comprising administering to a patient in need thereof a therapeutically effective amount of the ursolic acid derivative according to claim 1.

4. A method for inhibiting calcium channel activity in a patient, comprising administering an effective amount of the ursolic acid derivative according to claim 1 to the patient.

5. A method of making an ursolic acid derivative, comprising:
methylating the C3 hydroxyl group and the C28 acetoxy group of ursolic acid to produce a 3-methoxy ursolic methyl ester,
reducing the 3-methoxy ursolic methyl ester to produce an aldehyde derivative, and
reacting the aldehyde derivative with methyl acetoacetate and ammonia under refluxing conditions to produce the ursolic acid derivative having the structural formula

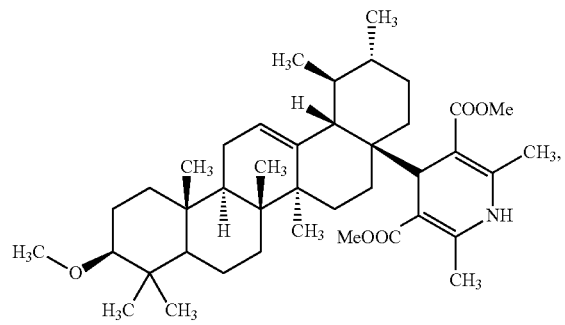

or a pharmaceutically acceptable salt thereof.

6. The method of claim 5, wherein the step of methylating the C3 hydroxyl group and the C28 acetoxy group of ursolic acid comprises reacting the ursolic acid with methyl iodide in dry acetone with potassium carbonate.

7. The method of claim 6, wherein the step of reacting the ursolic acid with methyl iodide in dry acetone with potassium carbonate is carried out by refluxing at a temperature ranging from about 25° C. to about 28° C. for at least 75 hours.

8. The method of claim 2, wherein the step of reducing the 3-methoxy ursolic methyl ester comprises adding potassium diisobutyl-t-butoxy aluminum hydride to the 3-methoxy ursolic methyl ester.

9. The method of claim 8, wherein, the 3-methoxy ursolic methyl ester is dissolved in tetrahydrofuran before adding potassium diisobutyl-t-butoxy aluminum hydride.

10. The method of claim 9, wherein the step of reacting the aldehyde derivative with methyl acetoacetate and ammonia under refluxing conditions comprises:
 forming a mixture of the aldehyde, methyl acetoacetate, ammonia and montmorillonite K10 in water to form a mixture;
 refluxing the mixture; and
 evaporating the refluxed mixture to obtain the ursolic acid derivative.

11. A pharmaceutical composition, comprising a compound having a structural formula of

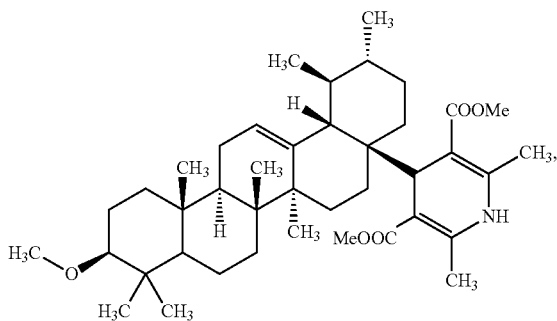

and a pharmaceutically acceptable carrier.

* * * * *